US007019120B2

United States Patent
Iyer et al.

(10) Patent No.: US 7,019,120 B2
(45) Date of Patent: Mar. 28, 2006

(54) CLOUD-POINT EXTRACTION OF ENZYMES AND POLYPEPTIDES FROM A FERMENTATION BROTH USING A NON-IONIC SURFACTANT

(75) Inventors: Prashant Iyer, Raleigh, NC (US); Kishore Rane, Raleigh, NC (US); Kevin S. Wenger, Wake Forest, NC (US); Fahd Azzabi, Chavannes (CH)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 10/734,431

(22) Filed: Dec. 12, 2003

(65) Prior Publication Data

US 2004/0147001 A1    Jul. 29, 2004

Related U.S. Application Data

(60) Provisional application No. 60/434,722, filed on Dec. 19, 2002.

(51) Int. Cl.
*C07K 1/14* (2006.01)
(52) U.S. Cl. ............... 530/422; 530/344; 435/183; 435/816; 210/767; 210/511
(58) Field of Classification Search ........ 435/816, 435/183; 210/767, 511, 634; 530/344, 422
See application file for complete search history.

(56) References Cited

U.S. PATENT DOCUMENTS 6,105,786 A    8/2000   Braunstein et al.

OTHER PUBLICATIONS

Terstappen et al, Journal of Biotechnology, 1993, vol. 28, p. 263-275.*

* cited by examiner

*Primary Examiner*—Leon B. Lankford, Jr.
*Assistant Examiner*—Allison M. Ford
(74) *Attorney, Agent, or Firm*—Elias J. Lambins; Jason I. Garbell

(57) ABSTRACT

A method of extracting a polypeptide of interest from a fermentation broth comprising:
  i) adjusting the pH close to pI of the polypeptide of interest;
  ii) adding a non-ionic surfactant with a hydrophile-lipophile balance (HLB) of 12 or lower;
  iii) cooling the mixture for solubilization and incubating at above cloud point for extraction;
  iv) phase separating at below cloud point to obtain liquid-liquid-solid fractions; and
  v) recovering the surfactant-rich top phase containing the polypeptide of interest.

16 Claims, No Drawings

CLOUD-POINT EXTRACTION OF ENZYMES AND POLYPEPTIDES FROM A FERMENTATION BROTH USING A NON-IONIC SURFACTANT

TECHNICAL FIELD

The present invention deals with extracting a polypeptide of interest from a whole or clarified fermentation broth in a very efficient way.

BACKGROUND ART

Surfactant based extraction for recovering enzymes is a field of active research both in academia and industry.

Phase separation using non-ionic surfactants but high amounts of salts (2 to 30% w/v) is claimed in, e.g., U.S. Pat. No. 6,105,786. Although salts are inexpensive, these processes may not be commercially attractive for large scale recovery of commodity products, primarily because of the huge environmental load such high amounts of salt would impose. Furthermore, corrosion could potentially be an issue needing an expensive material of construction.

An alternative is to induce phase separation using temperature. Traditional cloud point extraction (heating above the cloud point of non-ionic detergent with or without the aid of the centrifuge) do not work well for extracting proteins directly from fermentation broth containing high starting protein concentrations (typically obtained in industrial fermentations for commodity products). This is because of phase separation/disengagement problems due to high viscosity and low density difference of phases.

A new extraction process based on non-ionic surfactants has been developed and is described herein that is useful for recovering proteins in high yields directly from fermentation broth in a single step.

SUMMARY OF THE INVENTION

The inventors have found that it is possible to recover in high yields and simultaneously concentrate polypeptides of interest in one step directly from a fermentation broth by using the following method:
  i) adjusting the pH close to pI of the polypeptide of interest;
  ii) adding a non-ionic surfactant with a hydrophile-lipophile balance (HLB) of 12 or lower;
  iii) cooling the mixture for solubilization and incubating at above cloud point for extraction;
  iv) phase separating at below cloud point to obtain liquid-liquid-solid fractions; and
  v) recovering the surfactant-rich top phase containing the polypeptide of interest.

DETAILED DISCLOSURE OF THE INVENTION

The present invention deals with extracting a polypeptide of interest from a fermentation broth; in particular from a whole or clarified fermentation broth.

When using a whole fermentation broth as the starting material for the method of the invention, the fermentation broth may or may not be diluted. Often a dilution of 0 to 100% w/w (broth basis) with water is preferred; if the dilution is higher it may result in spending energy in concentrating the product later in the downstream processing.

When using a clarified fermentation broth, the fermentation broth is typically diluted with water (0 to 100% w/w broth basis) and flocculated; the cells are separated by any conventional means such as drum filtration or centrifugation, and the clarified fermentation broth is then used as the starting material for the method of the invention.

Polypeptide of Interest

The polypeptide of interest according to the invention may be a peptide or an enzyme.

A preferred peptide according to this invention contains from 5 to 100 amino acids; preferably from 10 to 80 amino acids; more preferably from 15 to 60 amino acids; even more preferably from 15 to 40 amino acids.

In a preferred embodiment, the method is applied to enzymes, in particular to hydrolases (class EC 3 according to Enzyme Nomenclature; Recommendations of the Nomenclature Committee of the International Union of Biochemistry).

In a particular preferred embodiment the following hydrolases are preferred:

Proteases: Suitable proteases include those of animal, vegetable or microbial origin. Microbial origin is preferred. Chemically modified or protein engineered mutants are included. The protease may be an acid protease, a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Preferred commercially available protease enzymes include ALCALASE™, SAVINASE™, PRIMASE™, DURALASE™, ESPERASE™, RELASE™ and KANNASE™ (Novozymes A/S), MAXATASE™, MAXACAL™, MAXAPEM™, PROPERASE™, PURAFECT™, PURAFECT OXP™, FN2™, and FN3™ (Genencor International Inc.). Peptidases: An example of a suitable peptidase is FLAVOURZYME™ (Novozymes A/S).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens*, *Pseudomonas sp.* strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include "LIPOLASE, LIPOLASE ULTRA™ and LIPEX™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105,106, 124,128, 133, 154, 156, 181, 188,190, 197, 202, 208, 209, 243, 264, 304, 305, 391, 408, and 444.

Commercially available amylases are DURAMYL™, TERMAMYL™, FUNGAMYL™, NATALASE™, TERMAMYL LC™, TERMAMYL SC™, LIQUIZYME-X™ and BAN™ (Novozymes A/S), RAPIDASE™ and PURASTAR™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME™, and CAREZYME™ (Novozymes A/S), CLAZINASE™, and PURADAX HA™ (Genencor International Inc.), and KAC-500(B)™ (Kao Corporation).

Oxidoreductases

Oxidoreductases that may be treated according to the invention include peroxidases, and oxidases such as laccases, and catalases.

Other preferred hydrolases are carbohydrolases including MANNAWAY™ (Novozymes A/S) and pectate lyase (e.g. BIOPREPARATION 3000™ (Novozymes A/S)). Other preferred enzymes are transferases, lyases, isomerases, and ligases.

Adjusting pH Close to pI of the Polypeptide of Interest

According to the present invention the pH is adjusted to a pH close to the pI of the polypeptide of interest after the fermentation broth has, optionally, been diluted with water. The pI of the polypeptide may be determined as known in the art, e.g., as described in "Protein Purification, Principles, High Resolution Methods and Applications. Ed. Jan-Christer Janson and Lars Rydén, 1989, VCH publishers. Chapter 13", or by using "precast polyacrylamide gels for analytical isoelectric focusing" from Pharmacia Biotec (Order number 80-1124-80).

The inventors have found that the pH may be adjusted to be in the range of (pH-pI) of −3 to +1; preferably the pH may be adjusted to be in the range of (pH-pI) of −2 to −1; in particular the pH may be adjusted to a value of 1.3 units below the isoelectric point of the polypeptide of interest.

The pH of the whole or the clarified fermentation broth may be adjusted by use of virtually any acid or base. The acid may be organic or inorganic. Some examples are hydrochloric acid, sulfuric acid, nitrous acid, phosphoric acid, acetic acid, citric acid and formic acid. Preferred acids are formic acid, citric acid, phosphoric acid or acetic acid; in particular formic acid.

Useful bases according to the invention are ammonium hydroxide, potassium hydroxide and sodium hydroxide; in particular potassium hydroxide.

Non-Ionic Surfactant with a Hydrophile-Lipophile Balance of 12 or Lower

After the pH adjustment a non-ionic surfactant with an hydrophile-lipophile balance (HLB) of 12 or lower is added to the fermentation broth at 5 to 25% (w/w at diluted fermentation broth basis); in particular at 10 to 15% (w/w at diluted fermentation broth basis).

The hydrophile-lipophile balance (HLB) of a given surfactant is determined by using the method described in, e.g., Becher, P., and Birkmeier, R. L., J. Am. Oil Chem. Soc. 41(1964): 169.

The inventors have found that the hydrophile-lipophile balance (HLB) of the non-ionic surfactant should preferably be in the range of from 7 to 12; even more preferably in the range of from 9 to 11.

The non-ionic surfactant according to the invention may preferably be selected from the group consisting of an alcohol ethoxylate, a fatty acid ester, a polyether alcohol and an amine oxide; in particular the non-ionic surfactant is a linear fatty alcohol ethoxylate with a narrow range degree of ethoxylation.

Ethoxylation can be achieved by the reaction of an alcohol with ethylene oxide. The ethoxylation can be influenced by the catalyst and by the choice of the alkyl group of the alcohol.

A narrow range ethoxylated alcohol, also called peaked ethoxylated alcohol, has an ethoxylation distribution curve that is narrower than the equivalent standard ethoxylate and contains considerably lower free alcohol. This gives the non-ionic surfactant focused properties and a very low odour especially when derived from short chain alcohol.

Examples of alcohol ethoxylates with a narrow range degree of ethoxylation are BEROL® 260 (narrow range C9–C 11 alcohol with 4EO), BEROL® 266 (narrow range C9–C 11 alcohol with 5.5EO), and BEROL® 840, all available from Akzo Nobel.

Solubilization/Incubating/Phase Separating

After the addition of the non-ionic surfactant the mixture is cooled for solubilization and incubated at a temperature above cloud point for extraction.

The mixture is cooled to 3–10° C. for solubilization; preferably to 4–6° C. for solubilization; in particular to 5° C. for solubilization. The mixture should be cooled and hold at the wanted temperature from 15 minutes to 3 hours; preferably at the wanted temperature from 30 minutes to 2 hours; more preferably at the wanted temperature from 45 minutes to 75 minutes; in particular at the wanted temperature for 1 hour.

After cooling the mixture is incubated at 2–10° C. above cloud point for extraction; preferably at 3–9° C. above cloud point for extraction. The mixture should be incubated at the wanted temperature from 15 minutes to 3 hours; preferably at the wanted temperature from 30 minutes to 2 hours; more preferably at the wanted temperature from 45 minutes to 75 minutes; in particular at the wanted temperature for 1 hour.

After the cloud point extraction a phase separating step takes place at a temperature below cloud point to obtain liquid-liquid-solid fractions. The phase separating step is preferably done at a temperature 2–15° C. below cloud point; preferably at a temperature 3–11° C. below cloud point. The phase separation may be done by any method known in the art, e.g. by centrifugation. The surfactant-rich top phase contains the polypeptide of interest. The aqueous phase may be recycled.

Cloud point: Cloud point may be determined experimentally by heating up a clear aqueous solution of 1% (w/w) surfactant until clouding of the solution occurs, and subsequent cooling down of this solution until clarification is observed again.

Cloud point may also be estimated from molecular structure of the surfactant as given in the reference Journal of colloid and interface science 193, 132–136 (1997) Article No. CS975053.

Further Recovery of the Polypeptide of Interest

A further aspect of the invention concerns the downstream processing of the polypeptide of interest after phase separation below cloud point.

The surfactant-rich phase containing the polypeptide of interest may be further recovered using standard technology, e.g. concentrated to a paste form; in particular it may be concentrated by vacuum evaporation. A concentration of up to 3x may often be appropriate. It may sometimes be an advantage to adjust the pH to neutral before the mixture is concentrated.

The polypeptide of interest may be stabilized and standardized as known in the art.

Surfactant Recycle

It is possible that the surfactant used in the recovery of some polypeptides of interest using the process described in the present invention may or may not be compatible with its ultimate end use. In such cases surfactant costs could be a major factor affecting economic recovery of proteins. For these cases, surfactant used for polypeptide extraction could be recycled using methods (such as organic solvent extraction followed by vacuum distillation) that are known in the art. Polypeptide back extracted into the aqueous phase could then be further concentrated or purified by conventional methods such as precipitation, ultrafiltration, chromatography or evaporation.

The invention is further illustrated in the following example which is not intended to be in any way limiting to the scope of the invention as claimed.

EXAMPLE 1

Enzyme

Two lipases were tested:

Lipase A: a recombinant *Humicola lipase* as described in EP 0 305 216 B1.

Lipase B: a recombinant *Humicola lipase* as described in WO 00/60063.

Surfactants

The polyoxyethylene detergent Agrimul NRE C12E05 (from Cognis Corporation formerly Henkel KGaA) was used. C12E05 is a non-ionic surfactant that contains a C12 linear alkyl chain and exhibits a narrow-range ethylene oxide distribution with an average of five ethylene oxide groups. The cloud point of C12O5 in 1% solution is 23° C. and its HLB is 9.25.

Fermentation Broths

The fermentation broths were first diluted 0 to 100% with tap water. Extraction pH was adjusted to desired levels using formic acid or KOH. Surfactant level was varied from 5–15% (dil. broth wt. basis). Mixtures were gently agitated at about 5° C. for 1 hr for solubilization. Mixtures were later heated in a water bath for 1 hr at 32° C. for extraction. The resulting solutions were centrifuged (using IEC Centra GP8R centrifuge equipped with temperature control) at 4000 rpm for 15 min at 12–15° C. for phase separation into liquid-liquid-solid fractions with surfactant rich top phase containing the enzyme.

Analytical

Lipase concentration in the phases was determined by measuring enzymatic activities. The enzymatic activity of lipases were expressed in KLU (Kilo Lipase Units) per gram of product. The activity of lipase is determined on a tributyrin substrate at 30° C./pH 7.0 in relation to an analytical standard.

Extraction Performance Parameters

Extraction performance was monitored by calculating partition coefficient, volume ratio, concentration factor and one-step recovery yields.

Partition coefficients were calculated as the ratio of the enzyme activity in the surfactant-rich top liquid phase to the enzyme activity in the surfactant-poor middle aqueous phase.

Volume ratio was defined as the ratio of surfactant-rich top phase to the total volume.

Concentration factor was calculated as the ratio of enzyme activity in the surfactant rich top phase to the starting enzyme activity of the mixture before surfactant addition.

One-step recovery yield was defined as the % of the original active enzyme in the fermentation broth that is recovered in the surfactant-rich top phase in a single step.

Surfactant Selection

Lipase A was extracted from diluted UF concentrate (a relatively pure enzyme system) using non-ionic surfactants with different HLB values: Triton X-100 (HLB 13.5), Triton X-114 (HLB 12.4), NRE C14E06 (HLB 10.5) and NRE C12E05 (HLB 9.25) under same conditions using cloud point extraction.

| Surfactant | HLB | One-step Recovered yield (%) |
|---|---|---|
| Triton X-100 | 13.5 | 13.3 |
| Triton X-114 | 12.4 | 22.8 |
| C14E06 | 10.5 | 51.6 |
| C12E05 | 9.25 | 60.7 |

Highest one-step recovery yield shown is 60.7% for surfactant with HLB of 9.25, but these screenings were done before the extraction process was optimized in accordance with the present invention. But the relative trends are nevertheless useful. From the data above, it can be seen that as the HLB of the surfactant decreases, the recovery yield may be enhanced. It is also apparent from the above data that an efficient recovery is possible by using a surfactant with HLB even as high as 10.5.

Effect of pH

The fermentation broth with lipase A was filtered through a rotary vacuum drum filter (RVDF).

40 g of filtrate was adjusted to pH 3.5, 4.8 and 6.5 using 10% solution of formic acid. NRE 1205 surfactant was added at a fixed level of 10 wt % (filtrate wt. basis, i.e., 4 g of surfactant was added). The mixture was gently agitated at about 5° C. for 1 hr for solubilization. The mixture was later heated in a water bath for 1 hr at 32° C. for extraction. The resulting solution was centrifuged (using IEC Centra GP8R centrifuge equipped with temperature control) at 4000 rpm for 15 min for phase separation into surfactant rich top phase and surfactant poor bottom aqueous phase. Results obtained are shown below.

| pH | Partition Coefficient | Conc. factor | One-step Yield (%) |
|---|---|---|---|
| 6.5 | 1.6 | 0.94 | 49.7 |
| 4.8 | 2.6 | 1.13 | 63.8 |
| 3.5 | 7.6 | 1.24 | 65.2 |

From the data set forth above, it can be seen that as the extraction pH is lowered, partition coefficient, concentration factor and one-step recovery yield all can be enhanced. In particular, extraction is favoured by adjusting the pH closer to pI (this enzyme has a pI of 4.8), preferably to a value of 1.3 units below isoelectric point. Whole broth extraction of lipase B (pI of 4.8) was carried out by first diluting the material with 100% of tap water, adding 10% NRE 1205 surfactant (dil. broth wt. basis) at two different pH levels of 4.8 and 3.5 (using the procedure described above). The results are shown below.

| pH | Partition Coefficient | Conc. factor | One-step Yield (%) |
|---|---|---|---|
| 4.8 | 1.9 | 1.27 | 58.9 |
| 3.5 | 5.8 | 1.64 | 82.3 |

Here again best results are obtained by adjusting the extraction pH to 1.3 units below pI.

Effect of Initial Broth Dilution

Broth viscosity may affect extraction performance.

Viscosity reduction can be achieved by broth dilution. The effect of initial broth dilution on extraction performance for lipase B was investigated at pH 3.5 and 10 wt % (% dil. broth basis) NRE 1205 surfactant addition using the procedure outlined above. The results are shown below.

| Broth dilution (% broth basis) | Partition Coefficient | One-step Yield (%) |
|---|---|---|
| 0% | 3.1 | 59.1 |
| 100% | 5.8 | 82.3 |

From the above data it is seen that it is possible to extract the enzyme directly without any broth dilution, but partition coefficient and one-step recovery yield can be enhanced by diluting the incoming broth by at least 100%.

Vacuum Evaporation After Phase Separation

Using the process described in the present invention it is possible to recover in high yields and simultaneously concentrate polypeptides of interest in one step directly from fermentation broth. But even higher protein concentration than the one produced in the surfactant-rich top phase may be achieved by adding a vacuum evaporation stage after extraction and phase separation.

Surfactant-rich phase was first obtained from lipase B broth extraction using 200 g broth, 200 g tap water, 15% (dil. broth basis) surfactant loading and the procedure described above. The pH of the top phase was adjusted to 7.5 from 3.5 using potassium hydroxide before evaporating at reduced pressure of 30 mbar and 45° C. in a Buchi Rotavapor (Model R-124). Desired set point was reached in a gradual fashion to prevent excessive foaming. The results obtained indicate that more than 3-fold increase in protein concentration is feasible with almost no loss of yields on evaporation.

The paste as it is may be transported to the detergent formulator where the paste may be reconstituted to any consistency by adding water.

Alternatively, the paste containing the detergent surfactant and the enzyme may be directly used to make a flowable, granular detergent powder.

The invention claimed is:

1. A method of extracting a hydrophobic polypeptide of interest from a fermentation broth comprising:
   i) adjusting the pH of the hydrophobic polypeptide of interest to a pH in the range of 3 pH units less than the pI of the hydrophobic polypeptide of interest to 1 pH unit greater than the pI of the hydrophobic polypeptide of interest;
   ii) adding a non-ionic surfactant with a hydrophile-lipophile balance (HLB) of 12 or lower;
   iii) cooling the mixture of the hydrophobic polypeptide of interest and the non-ionic surfactant for solubilization and incubating at above cloud point for extraction;
   iv) phase separating at below cloud point to obtain liquid-liquid-solid fractions; and
   v) recovering the surfactant-rich top phase containing the hydrophobic polypeptide of interest.

2. The method according to claim 1, wherein the hydrophobic polypeptide of interest is an enzyme.

3. The method according to claim 2, wherein the enzyme is selected from the group consisting of a protease, an amylase, a cellulase, a lipase, an oxidoreductase, and a carbohydrolase.

4. The method according to claim 1, wherein the hydrophobic polypeptlde of interest contains from 5 to 100 amino acids.

5. The method according to claim 1, wherein step i) comprises adjusting the pH of the hydrophobic polypeptide of interest to a pH in the range of 2 pH units less than the pI of the hydrophobic polypeptide of interest to 1 pH unit less than the pI of the hydrophobic polypeptide of interest.

6. The method according to claim 1, wherein step i) comprises adjusting the pH of the hydrophobic polypeptide of interest to a pH of 1.3 units below the isoelectric point of the hydrophobic polypeptide of interest.

7. The method according to claim 1, wherein the hydrophile-lipophile balance (HLB) is in the range of from 7 to 12.

8. The method according to claim 1, wherein the non-ionic surfactant is selected from the group consisting of an alcohol ethoxylate, a fatty acid ester, a polyether alcohol and an amine oxide.

9. The method according to claim 1, wherein the non-ionic surfactant is a linear fatty alcohol ethoxylate.

10. The method according to claim 1, wherein the non-ionic surfactant is added in an amount of 5 to 25% (w/w).

11. The method according to claim 1, wherein the mixture is cooled to 3–10° C. for solubilization.

12. The method according to claim 1, wherein the mixture is incubated at 2–10° C. above cloud point for extraction.

13. The method according to claim 1, wherein the phase separating is done at 2–15° C. below cloud point for extraction.

14. The method according to claim 1, additionally comprising a step vi) of concentrating the extracted mixture to a paste form.

15. The method according to claim 14, wherein in step vi) the extracted mixture is concentrated to a paste form after adjusting the pH to neutral.

16. The method according to claim 1, wherein in step i) the fermentation broth is diluted (0 to 100%) for viscosity reduction before adjusting the pH.

* * * * *